(12) United States Patent
Tonelli et al.

(10) Patent No.: US 9,394,243 B2
(45) Date of Patent: Jul. 19, 2016

(54) (PER)FLUOROPOLYETHER BLOCK COPOLYMERS

(75) Inventors: Claudio Adolfo Pietro Tonelli, Paderno D'adda (IT); Simonetta Antonella Fontana, Milan (IT); Marco Galimberti, Bollate (IT); Piero Gavezotti, Milan (IT)

(73) Assignee: SOLVAY SPECIALTY POLYMERS ITALY S.P.A., Bollate (Milan) (IT)

( * ) Notice: Subject to any disclaimer, the term of this patent is extended or adjusted under 35 U.S.C. 154(b) by 0 days.

(21) Appl. No.: 14/128,020

(22) PCT Filed: Jun. 20, 2012

(86) PCT No.: PCT/EP2012/061782
§ 371 (c)(1),
(2), (4) Date: Dec. 20, 2013

(87) PCT Pub. No.: WO2012/175534
PCT Pub. Date: Dec. 27, 2012

(65) Prior Publication Data
US 2014/0135244 A1 May 15, 2014

(30) Foreign Application Priority Data

Jun. 24, 2011 (EP) .................................... 11171363

(51) Int. Cl.
| | |
|---|---|
| C08G 65/22 | (2006.01) |
| C07C 271/24 | (2006.01) |
| C07C 269/02 | (2006.01) |
| C07C 41/22 | (2006.01) |
| C07C 43/12 | (2006.01) |
| C07C 55/32 | (2006.01) |
| C07C 67/00 | (2006.01) |
| C07C 69/708 | (2006.01) |
| C08G 65/00 | (2006.01) |

(52) U.S. Cl.
CPC ............... *C07C 271/24* (2013.01); *C07C 41/22* (2013.01); *C07C 43/126* (2013.01); *C07C 55/32* (2013.01); *C07C 67/00* (2013.01); *C07C 69/708* (2013.01); *C07C 269/02* (2013.01); *C08G 65/007* (2013.01)

(58) Field of Classification Search
CPC ........................................................ C08G 65/22
USPC ................................... 528/402; 508/509, 582
See application file for complete search history.

(56) References Cited

U.S. PATENT DOCUMENTS

| | | | |
|---|---|---|---|
| 3,847,978 A | 11/1974 | Sianesi et al. | |
| 4,755,330 A | 7/1988 | Viola et al. | |
| 4,845,268 A * | 7/1989 | Ohsaka et al. | ................. 560/184 |
| 4,904,417 A | 2/1990 | Ohsaka et al. | |
| 4,973,742 A * | 11/1990 | Ohsaka et al. | ................. 560/184 |
| 6,136,331 A | 10/2000 | Morita et al. | |
| 6,919,479 B2 | 7/2005 | Di Meo et al. | |
| 7,132,574 B2 | 11/2006 | Picozzi et al. | |
| 2006/0281946 A1 | 12/2006 | Morita et al. | |

FOREIGN PATENT DOCUMENTS

| | | |
|---|---|---|
| EP | 148482 A2 | 7/1985 |
| EP | 2151239 A1 | 2/2010 |
| EP | 2221664 A1 | 8/2010 |
| JP | 2003231719 A | 8/2003 |
| JP | 2009173644 A | 8/2009 |
| JP | 2009215555 A | 9/2009 |

* cited by examiner

*Primary Examiner* — Duc Truong

(57) ABSTRACT

The invention relates to (per)fluoropolyether block copolymers comprising: A) a fluoropolyoxyalkylene segment (chain $R_a$) comprising one or more units of formula ($CHXCF_2CF_2O$)— in which X is hydrogen or fluorine; B) a (per)fluoropolyoxyalkylene segment (chain Rf), that is to say a segment comprising recurring units having at least one catenary ether bond and at least one fluorocarbon moiety, said (per)fluoropolyoxyalkylene segment being different from chain $R_a$ and having a molecular weight higher than 400 g/mol. These copolymers are endowed with improves lubricant properties or with improved water and oil-repellence properties.

4 Claims, No Drawings

(PER)FLUOROPOLYETHER BLOCK COPOLYMERS

This application is a U.S. national stage entry under 35 U.S.C. §371 of International Application No. PCT/EP2012/061782 filed Jun. 20, 2012, which claims priority to European Application No. 11171363.2, filed on Jun. 24, 2011. The entire contents of these applications are explicitly incorporated herein by this reference.

TECHNICAL FIELD

The present invention relates to (per)fluoropolyether (PFPE) block copolymers, in particular to (per)fluoropolyether block copolymers containing segments that can be obtained by ring-opening reaction of 2,2,3,3-tetrafluorooxethane with a (per)fluoropolyether.

BACKGROUND ART

EP 0148482 A (DAIKIN IND LTD) relates to halogen-containing PFPEs which are said to be suitable for a variety of uses, e.g. lubricants. This document discloses, inter alia, a halogen-containing PFPE having formula [formula (XII) on page 5, lines 18-26]:

$$A(CH_2CF_2CF_2O)_p[CF(CF_3)CF_2O]_qCF(CF_3)COF$$

wherein:
p is an integer of 2 to 200 and q is an integer of 0 to 50 and A is F, Br, I or it can be a group of formula:

$R_fCF_2O$— or a group of formula:

$R'_fO$—$(CF(CF_3)CF_2O)_{p+1}$ in which $R_f$ and $R'_f$ can represent a perfluoroalkyl group having from 1 to 10 carbon atoms and p is an integer of 0 to 50 [formulae (VIII) and (IX) on page 4, lines 19-22].

U.S. Pat. No. 4,904,417 (DAIKIN IND LTD) discloses the reaction of compounds of formula A-$(CF_2CF_2)_m$-A', wherein m is an integer from 1 to 6 and A and A' are, possibly, COF, with 2,2,3,3-tetrafluorooxethane in the presence of fluoride anions as polymerization initiators, to yield derivatives having COF end groups.

U.S. Pat. No. 6,136,331 (DAIKIN IND LTD) U.S. Pat. No. 6,136,331 to Daikin discloses cosmetic compositions comprising compounds of formula $XO$—$[CF(CF_3)_2O]_h$—$(CF_2CF_2O)_o$—$Y$—$COOR_3$, wherein h+o ranges from 1 to 100, X can be H, F, Cl, Br, or at least partially fluorinated alkyl group, Y is a partially or completely fluorinated alkyl group, and $R^3$ is a $C_1$-$C_{22}$ aliphatic group. These compounds can be notably manufactured by reaction of a hexafluoropropylene oxide oligomer having acyl fluoride end groups and 2,2,3,3-tetrafluorooxethane in the presence of a catalyst, and subsequent reaction of the compound obtained therefrom to derivatize the COF end group with an alcohol compound or by fluorination. The catalyst can be notably KF, CsF. Preparative example 5 discloses, for instance, the reaction of a HFPO dimer $[C_3F_7O$—$CF(CF_3)FCOF]$ with 2,2,3,3-tetrafluorooxethane and CsF and subsequent reaction with methanol to yield a compound of formula: $C_3F_7OC(CF_3)FCF_2O$—$(CH_2CF_2CF_2O)_n$—$CH_2CF_2$—$COOCH_3$ with n~10.

JP 2003231719 (DAIKIN IND LTD) discloses certain fluoroelastomers comprising recurring units derived from particular vinyl ether compounds; among the synthetic methods used in the exemplified working embodiments of this application for manufacturing said recurring units, use is made of the reaction of 2,2,3,3-tetrafluorooxethane to provide acyl fluoride compounds, more precisely I—$CH_2CF_2$—COF and Cl—$CH_2CF_2$—COF.

US 2006281946 (DAIKIN IND LTD) describes the synthesis of compounds of formula: $Rf_1$—$(OCH_2CF_2CF_2)_{n1}OCX_1X_2CF_2(Rf_2)_{n2}$—COOM wherein $Rf^1$ is a straight or branched fluoroalkyl group containing 1 to 20 carbon atoms, optionally containing 1 to 5 oxygen atoms in the main chain, by ring-opening polymerization reaction of an acyl fluoride derivative of formula $Rf_3$—COF with 2,2,3,3-tetrafluorooxethane, wherein $Rf_3$ is a straight or branched fluoroalkyl group containing 1 to 20 carbon atoms, optionally containing 1 to 5 oxygen atoms in the main chain.

Similarly, JP 2009173644 (DAIKININD LTD) discloses a method for manufacturing compounds of formula: $Rf_1$—$(OCH_2CF_2CF_2)_{n1}OCX_1X_2CF_2(Rf_2)_{n2}$—COOM by ring-opening polymerization of 2,2,3,3-tetrafluorooxethane onto an acyl fluoride derivative of formula $Rf_3$—COF, wherein $Rf_3$ is a fluoroalkyl group optionally containing 1-5 oxygen atoms.

None of the above documents discloses or suggests to prepare block copolymers using acyl fluorides of (per)fluoropolyethers complying with certain molecular weight requirements as precursors to be used as oils with improved anti-wear properties or with improved hydrophobic or oilophobic properties.

SUMMARY OF INVENTION

It has now been found that certain block copolymers comprising (per)fluoropolyether segments having a molecular weight higher than 400 g/mol are endowed with improved anti-wear properties or with improved hydrophobic or oilophobic properties.

Accordingly, the present invention relates to a (per)fluoropolyether block copolymer comprising:
A) a fluoropolyoxyalkylene segment (chain $R_a$) comprising one or more units of formula $(CHXCF_2CF_2O)$— in which X is hydrogen or fluorine;
B) a (per)fluoropolyoxyalkylene segment (chain $R_f$), that is to say a segment comprising recurring units having at least one catenary ether bond and at least one fluorocarbon moiety, said (per)fluoropolyoxyalkylene segment being different from chain $R_a$ and having a molecular weight higher than 400 g/mol.

For the purposes of the present description, the expression "(per)fluorinated segment" means that the segment may be fully or partially fluorinated. Likewise, the expression "perfluoro(oxy)alkyl group" reported below is intended to mean a perfluoroalkyl group containing catenary ether bonds.

The (per)fluoropolyoxyalkylene segment (chain $R_f$) is preferably a chain comprising recurring units having general formula —$(CF_2)_k$—CFZ—O—, wherein k is an integer of from 0 to 3 and Z is selected between a fluorine atom and a $C_1$-$C_6$ perfluoro(oxy)alkyl group.

More preferably, chain $R_f$ complies with formula:

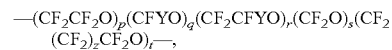

—$(CF_2CF_2O)_p(CFYO)_q(CF_2CFYO)_r(CF_2O)_s(CF_2(CF_2)_zCF_2O)_t$—, the recurring units being statistically distributed along the (per)fluoropolyoxyalkylene chain, wherein:
Y is a $C_1$-$C_5$ perfluoro(oxy)alkyl group;
z is 1 or 2;
p, q, r, s, t are integers ≥0, selected in such a way as to comply with the above-mentioned molecular weight requirement.

Even more preferably, chain $R_f$ complies with formula:

—$(CF_2CF_2O)_p(CF_2O)_q$—, wherein:

p' and q' are integers ≥0 and are selected in such a way as they comply with the above-mentioned molecular weight requirement; still more preferably, the p/q or p'/q' ratio is 2.

In a first aspect, the block copolymer of the invention preferably complies with formula (IA) below:

$$R_a—R_f—R_{a'} \quad (IA)$$

in which chain $R_f$ is as defined above and chain $R_a$ is selected from any one of groups (II)-(VI) as defined further below and $R_{a'}$ is the same as $R_a$ or is a $(C_1-C_5)$(per)fluoroalkyl group optionally containing hydrogen and/or chlorine atoms. In the following, the block copolymers complying with formula (IA) above will be referred to either as block copolymers of formula (IA), or block copolymers (IA), or compounds of formula (IA) or compounds (IA).

Group (II) complies with formula:

$$(CH_2CF_2CF_2O)_nCH_2CF_2C(O)F \quad (II)$$

wherein n is an integer equal to or higher than 1, preferably comprised between 1 and 100, more preferably comprised between 5 and 15.

Group (III) complies with formula:

$$(CH_2CF_2CF_2O)_nCH_2CF_2C(O)R \quad (III)$$

wherein:

n is as defined above and

R is hydrogen, a hydroxy group or a $W—R^1$ group. In group $W—R^1$, W is a bond or is selected from —O—, —OC(O)—, —NHC(O)—, —NH—, —NR$^{1'}$—, wherein R$^{1'}$ is a straight or branched $C_1$-$C_6$ alkyl group, and $R^1$ is selected from: a straight or branched, saturated or unsaturated $(C_1-C_{36})$hydrocarbon chain; a $(C_5-C_{14})$cycloalkyl or a $(C_5-C_{14})$cycloalkyl$(C_1-C_{10})$alkyl group, the cycloalkyl moiety being optionally substituted with one or more $(C_1-C_4)$straight or branched alkyl chains; a $(C_6-C_{14})$aryl or a $(C_1-C_{10})$alkyl$(C_6-C_{14})$aryl group and a group of formula —$R^A$—$CR_H$=$CH_2$ in which $R_H$ is hydrogen or a $(C_1-C_{34})$straight or branched, saturated or unsaturated hydrocarbon chain and $R^A$ is selected from:

—NH—$R^B$—O—CO— (j);

—NH—$R^B$—NHCOO—$R^B$—OCO— (jj);

—$R^B$—O—CO— (jjj);

$R^B$ being a divalent group selected from: a $(C_1-C_{10})$aliphatic group, a $(C_5-C_{14})$cycloaliphatic group, a $(C_6-C_{14})$aromatic or a $(C_1-C_{10})$alkyl$(C_6-C_{14}$ aryl) group.

Group (IV) complies with formula:

$$(CH_2CF_2CF_2O)_nCH_2CF_2CH_2OR' \quad (IV)$$

wherein n is as defined above and R' is hydrogen or a $(CHR^2CHR^3O)_m$—$R^4$ group in which:

$R^2$ and $R^3$ are both hydrogen or one is hydrogen and the other is methyl;

m is 0 or an integer equal to or higher than 1;

$R^4$ is selected from:

hydrogen, with the proviso that, when m is 0, $R^4$ is not hydrogen;

a straight or branched, saturated or unsaturated $(C_1-C_{36})$ hydrocarbon chain; a $(C_5-C_{14})$cycloaliphatic or a $(C_1-C_{10})$alkyl$(C_5-C_{14})$cycloalkyl group; a $(C_6-C_{14})$aromatic or a $(C_1-C_{10})$alkyl$(C_6-C_{14})$aromatic group;

a $P(O)R^5R^6$ group, in which $R^5$ and $R^6$ are, independently of each other, selected from hydroxy and —O$^-$X$^+$ groups, in which X$^+$ is selected from Li$^+$, Na$^+$, K$^+$, (NH$_3$R')$^+$, (NH$_2$R'R'')$^+$ and (NHR'R''R''')$^+$ wherein R is H or a linear or branched $(C_1-C_{22})$alkyl group optionally containing one or more —OH groups, and R', R'' and R''', equal to or different from each other, are linear or branched $(C_1-C_{22})$alkyl groups optionally containing one or more —OH groups or optionally linked to each other to form N-heterocyclic groups;

a COR$^7$ group, in which R$^7$ is a straight or branched, saturated or unsaturated $(C_1-C_{36})$hydrocarbon chain, preferably a —CR$_H$=CH$_2$ chain, wherein R$_H$ is hydrogen or a straight or branched, saturated or unsaturated $(C_1-C_{34})$ hydrocarbon chain, or R$^7$ is a $(C_5-C_{14})$cycloaliphatic or a $(C_1-C_{10})$alkyl$(C_5-C_{14})$cycloalkyl group; a $(C_6-C_{14})$ aromatic or a $(C_1-C_{10})$alkyl$(C_6-C_{14})$aromatic group;

a CONHR$^8$ group, in which R$^8$ is the same as R$^7$ or a COR$^7$ group, in which R$^7$ is as defined above;

a CO—$R^A$—$CR_H$=CH$_2$ group, wherein $R_H$ is hydrogen or a straight or branched, saturated or unsaturated $(C_1-C_{34})$hydrocarbon chain and $R_A$ is selected from the group consisting of:

—NH—$R^B$—O—CO— (j);

—NH—$R^B$—NHCOO—$R^B$—OCO— (jj);

—$R^B$—O—CO— (jjj);

$R^B$ being a divalent group selected from a $(C_1-C_{10})$aliphatic group, a $(C_5-C_{14})$cycloaliphatic group, a $(C_6-C_{14})$aromatic or a $(C_1-C_{10})$aliphatic$(C_6-C_{14})$aromatic group.

Group (V) complies with formula:

$$(CHYCF_2CF_2O)_nCHYCF_3 \quad (V)$$

wherein n is as defined above and Y is fluorine or hydrogen.

Group (VI) complies with formula:

$$(CH_2CF_2CF_2O)_nCH_2CF_2H \quad (VI)$$

wherein n is as defined above.

In a second aspect, the block copolymer of the invention preferably complies with formula (IB):

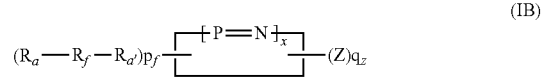

in which:

$R_f$ is as defined above;

$R_a$ is a group of formula $(CH_2CF_2CF_2O)_nCH_2CF_2CH_2O$ $(CHR^2CHR^3O)_m$ in which $R^2$ and $R^3$ are as defined above and m is 0 or an integer equal to or higher than 1;

$R_{a'}$ is the same as $R_a$ or is a $(C_1-C_5)$(per)fluoroalkyl group;

Z is a polar group of formula —O$^-$ M+, wherein M is selected from hydrogen, a monovalent metal, preferably an alkali metal selected from Li, Na, K, an ammonium radical selected from NR$_a$R$_b$R$_c$R$_d$, wherein each of R$_a$, R$_b$, R$_c$ and R$_d$ is, independently, a hydrogen atom or a $(C_1-C_{22})$hydrocarbon group, optionally fluorinated, or a polar group of formula —O$^-$)$_2$M'$^{2+}$, wherein M' is a divalent metal, preferably an alkaline earth metal selected from Ca and Mg;

x is 3 or 4, with the proviso that:

when x is 3, $p_f$ is an integer from 1 to 6, $q_z$ is 0 or an integer from 1 to 5 and $p_f$+$q_z$ is 6;

when x is 4, $p_f$ is an integer from 1 to 8, $q_z$ is 0 or an integer from 1 to 7 and $p_f$+$q_z$ is 8 and with the proviso that, when $R_{a'}$ is a $C_1$-$C_5$(per)fluoroalkyl group, $p_f$ is 1.

In a third aspect, the block copolymers of the invention preferably further comprise a block deriving from a diol or a diamine; more preferably, the invention comprises (per)fluoropolyether block copolymers of formula (IA) as defined above in which one or both of chain $R_a$ and $R_{a'}$ are linked to a diol compound of formula HO—$R_{diol}$—OH through an urethane or an ester moiety. The copolymers according to this third aspect of the invention will be herein after referred to also as compounds (IC).

In a compound of formula HO—$R_{diol}$—OH, $R_{diol}$ is a $C_2$-$C_{14}$ hydrocarbon group, optionally containing one or more cycloaliphatic or aromatic groups and/or additional functional groups. Examples of diols of formula HO—$R_{diol}$—OH are disclosed in EP 2151239 A (SOLVAY SOLEXIS).

According to a preferred aspect of the invention, additional functional groups in $R_{diol}$ are ionisable anionic and/or cationic groups, i.e. groups which, under appropriate pH conditions, form anionic or cationic groups.

For the purposes of the present invention, suitable ionisable anionic groups are, for example, carboxylic acid groups of formula —COOH, sulphonic acid groups of formula —$SO_3H$, phosphoric acid groups of formula —$PO_4H_2$, while suitable ionisable cationic groups are amine groups, which may be either comprised in the $R_{doil}$ backbone, according to formula —N($R_N$)—, wherein $R_N$ is selected from H and hydrocarbon groups having 1 to 6 carbon atoms, or comprised in side groups having formula —N($R_{N1}$)($R_{N2}$), wherein $R_{N1}$ and $R_{N2}$, equal to or different from one another, are independently selected from hydrogen and hydrocarbon groups containing from 1 to 6 carbon atoms.

A first preferred example of an $R_{diol}$ containing ionisable groups is a carboxylic-containing chain (R'$_{HC}$):

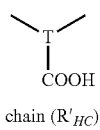

chain (R'$_{HC}$)

wherein T is a hydrocarbon trivalent group selected from a linear or branched $C_1$-$C_{12}$ hydrocarbon chain, a $C_3$-$C_{12}$ cycloaliphatic group or a $C_6$-$C_{12}$ aromatic group. More preferably, an (R'$_{HC}$) chain is selected from any one of the followings:

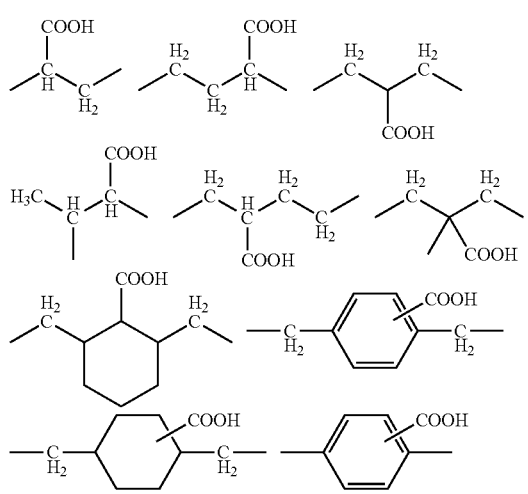

Even more preferably, chain (R'$_{HC}$) complies with formula:

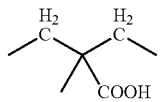

A second preferred example of an $R_{doil}$ containing an ionisable group is an amine-containing chain (R"$_{HC}$):

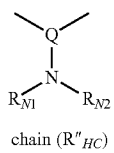

chain (R"$_{HC}$)

wherein $R_{N1}$ and $R_{N2}$ have the same meanings as defined above, Q is an hydrocarbon trivalent group selected from a linear or branched $C_2$-$C_{12}$ hydrocarbon chain, a $C_3$-$C_{12}$ cycloaliphatic group or a $C_6$-$C_{12}$ aromatic group. Chain (R"$_{HC}$) preferably complies with formula:

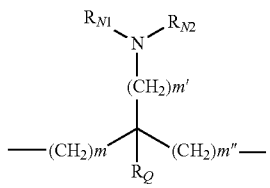

wherein $R_{N1}$ and $R_{N2}$ have the same meanings as defined above; more preferably, $R_{N1}$ and $R_{N2}$ are independently selected from linear or branched $C_1$-$C_4$ alkyl groups; m, m' and m" are 0 or an integer from 1 to 4, with the proviso that at least one of m and m" is not zero and $R_Q$ is H or a linear or branched $C_1$-$C_4$ alkyl group. Preferred amine-containing chains (R"$_{HC}$) are those of formulae —CH($CH_2$—N($C_2H_5$)$_2$)—$CH_2$— and —CH($CH_2$—N($CH_3$)$_2$)—$CH_2$—.

A third preferred example of an $R_{diol}$ containing an ionisable group is an amine-containing chain (R'''$_{HC}$)

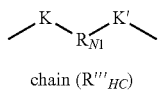

chain (R'''$_{HC}$)

wherein $R_{N1}$ has the same meanings defined above; preferably, $R_{N1}$ is selected from $C_1$-$C_4$ alkyl groups and K and K' are divalent hydrocarbon groups having from 1 to 6 carbon atoms.

A preferred group of block copolymers (IC) is the one in which the block deriving from an HO—$R_{diol}$—OH is linked to a chain $R_a$ or to chains $R_a$ and $R_{a'}$ through a urethane moiety complying with formula:

(II)

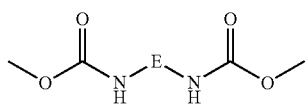

wherein E is a divalent hydrocarbon group, linear or branched, preferably a $C_1$-$C_{12}$ hydrocarbon group, optionally comprising one or more $C_3$-$C_{12}$ cycloaliphatic or $C_6$-$C_{12}$ aromatic groups. Preferably, group E is selected from any one of the following:

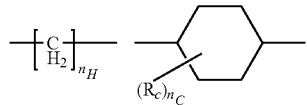

through a urethane moiety can be prepared by reacting a compound of formula (IA) as defined above in which one or both of $R_a$ and $R_{a'}$ are groups (IV) as defined above in which R' is hydrogen with a diisocyanate ONC-E-CNO, in which E is as defined above, followed by reaction with at least one one diol of formula HO—$R_{diol}$—OH, wherein $R_{diol}$ has the same meanings as defined above. A most particularly preferred group of copolymers according to this embodiment of the invention complies with formula (IC'):

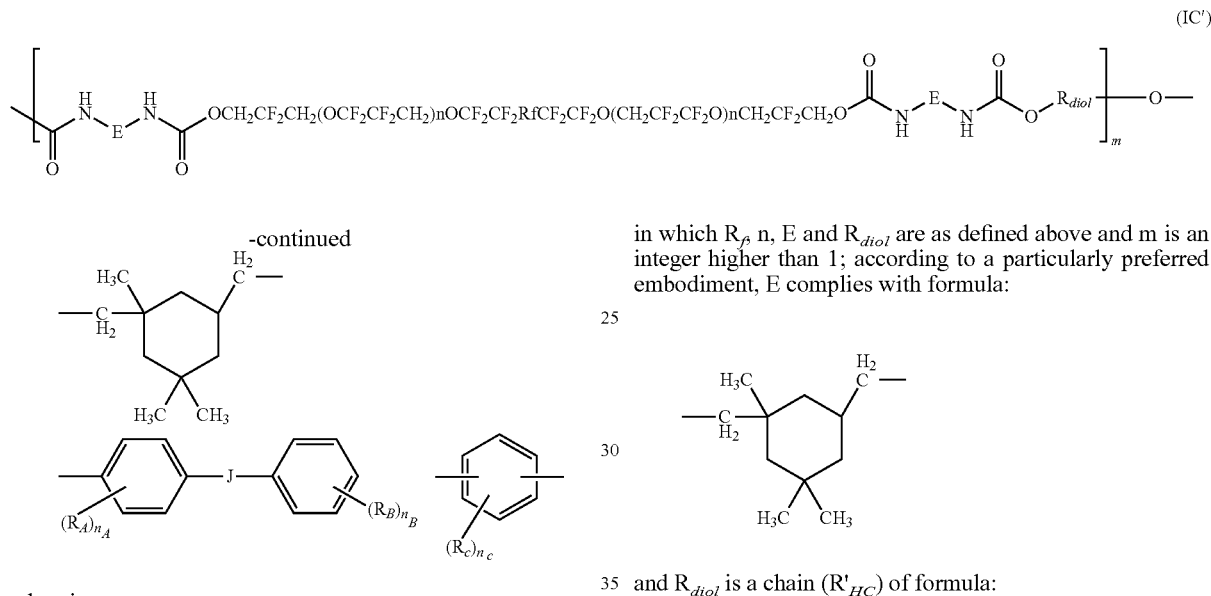

(IC')

-continued

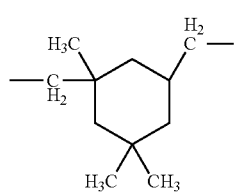

wherein:
- $n_H$ is an integer from 1 to 12, preferably equal to 6;
- J is a divalent bridging group selected from: a single bond; a methylene group (—$CH_2$—); an oxygen atom (—O—); a —$C(CH_3)_2$— group; a —$C(CF_3)_2$— group; a —$SO_2$— group; a —C(O)— group; preferably J is a methylene group;
- each of $R_A$, $R_B$, $R_C$ and $R_D$, equal or different at each occurrence, is independently a halogen atom (e.g. Cl, Br, F), a $C_1$-$C_6$ hydrocarbon group (e.g. methyl, ethyl), a substituent group like notably —$OR_H$, —$NR_{H'}R_{H''}$, —C(O)—$R_{H'''}$, wherein $R_H$, $R_{H'}$, $R_{H''}$ and $R_{H'''}$, equal to or different from each other, are independently at each occurrence a hydrogen atom or a $C_1$-$C_6$ hydrocarbon group;
- $n_A$, $n_B$ and $n_D$ are independently integers comprised between 0 and 4;
- $n_C$ is an integer comprised between 0 and 10.

Even more preferably, group E complies with formula:

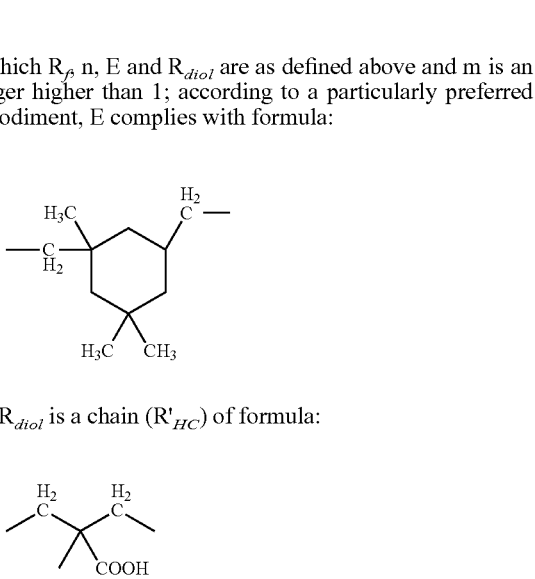

in which $R_f$, n, E and $R_{diol}$ are as defined above and m is an integer higher than 1; according to a particularly preferred embodiment, E complies with formula:

and $R_{diol}$ is a chain ($R'_{HC}$) of formula:

or is a chain ($R''_{HC}$) of formula:

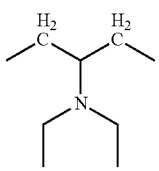

Preferred compounds of formulae (IA)-(IC) are those in which chain $R_f$ complies with formula —($CF_2CF_2O$)$_{p'}$($CF_2O$)$_{q'}$—, wherein p' and q' are integers ≥0 and are selected in such a way as they comply with the above-mentioned molecular weight requirement. More preferably, the p'/q' ratio is 2.

Preferred compounds of formulae (IA)-(IC) are also those in which $R_{a'}$ is the same as $R_a$ or those in which chain $R_{a'}$ differs from chain $R_a$ only the number of $CHXCF_2CF_2O$— units.

Preferred compounds of formulae (IA)-(IC) are also those in which n ranges from 1 to 100, preferably from 1 to 50, even more preferably from 5 to 15.

Block copolymers (IC) in which a block deriving from an HO—$R_{diol}$—OH is linked to a chain $R_a$ or to chains $R_a$ and $R_{a'}$ A first particularly preferred group of compounds of formula (IA) are those in which one or both chains $R_a$ or $R_{a'}$ contain an acrylate function. In this group of compounds, particularly preferred those in which:

chain $R_f$ complies with formula —$(CF_2CF_2O)_{p'}(CF_2O)_{q'}$—, wherein p' and q' are integers ≥0 and are selected in such a way as they comply with the above-mentioned molecular weight requirement;

$R_a$ is selected from: a group (IV) as defined above in which n ranges from 5 to 15 and R' is a $(CHR^2CHR^3O)_m$—$R^4$ group in which $R^4$ is a CO—$R_A$—$CR_H$=$CH_2$ group as defined above, wherein $R^A$ is a group of formula (j);

$R_{a'}$ is the same as a $R_a$.

A second particularly preferred group of block copolymers of formula (IA) is the one in which:

chain $R_f$ complies with formula —$(CF_2CF_2O)_{p'}(CF_2O)_{q'}$—, wherein p' and q' are integers ≥0 and are selected in such a way as they comply with the above-mentioned molecular weight requirement;

$R_a$ is a group (V) as defined above in which n ranges from 5 to 15; and $R_{a'}$ is the same as $R_a$.

A third particularly preferred group of block copolymers of formula (IA) is the one in which:

chain $R_f$ complies with formula —$(CF_2CF_2O)_{p'}(CF_2O)_{q'}$—, wherein p' and q' are integers ≥0 and are selected in such a way as they comply with the above-mentioned molecular weight requirement;

chain $R_a$ is a group of formula (VI) as defined above in which n ranges from 5 to 15; and $R_{a'}$ is the same as $R_a$.

The compounds of formula (IA) in which one or both of $R_a$ and $R_{a'}$ are groups (II) can be prepared by ring-opening reaction of 2,2,3,3-tetrafluorooxethane in the presence of organic or inorganic fluorides. For the purposes of the present invention, the expression "ring-opening reaction" means a reaction whereby 2,2,3,3-tetrafluorooxethane undergoes oligo- or polymerization. Typically, this reaction is carried out by reacting an acyl fluoride of a (per)fluoropolyether comprising an $R_f$ chain as defined above with 2,2,3,3-tetrafluorooxethane in the presence of an organic or inorganic fluoride. Examples of organic fluorides are alkylammonium fluorides, such as tetrabutylammonium fluoride, while examples of inorganic fluorides are lithium fluoride, sodium fluoride, potassium fluoride, calcium fluoride, barium fluoride, magnesium fluoride and cesium fluoride; according to a preferred embodiment, the metal fluoride is cesium fluoride. The reaction is usually carried out in an aprotic solvent, such as acetonitrile, or a glycol dialkyl ether; among glycol dialkyl ethers, diglyme and tetraglyme are preferred. The reaction is preferably carried out at a temperature ranging from about −30° C. to about +30° C., more preferably from about −5° C. to about +10° C., even more preferably at about 0° C. The reaction product, i.e. the compound in which one or both of $R_a$ and $R_{a'}$ are groups (II), i.e. groups which contain one or two acyl fluoride terminals, is useful as intermediate for the preparation of further preferred neutral or functionalized block copolymers of the invention, in particular for the preparation of the compounds of formula (IA) in which one or both of $R_a$ and $R_{a'}$ are any one of groups (III)-(VI).

In particular, for the preparation of the compounds of formula (IA) in which one or both of $R_a$ and $R_{a'}$ are groups (III) in which R is a hydroxy group, a block copolymer of formula (I) in which one or both of $R_a$ and $R_{a'}$ are groups (II) is submitted to hydrolysis, while for the preparation of the compounds of formula (IA) in which one or both of $R_a$ and $R_{a'}$ are groups (III) wherein R is a W—$R^1$ group in which W is O and $R^1$ is as defined above, a compound of formula (II) is reacted with an alcohol $R^1$OH, wherein $R^1$ is as defined above.

The compounds of formula (IA) in which one or both of $R_a$ and $R_{a'}$ are groups (III) in which R is hydrogen can be prepared according to conventional methods for the preparation of aldehydes, for example by catalytic reduction or by reduction with hydrides of a compound of formula (IA) in which one or both of $R_a$ and $R_{a'}$ are groups (III) wherein R is a W—$R^1$ group in which W is O and $R^1$ is hydrogen or an alkyl group, typically a $C_1$-$C_4$ alkyl group.

The compounds of formula (IA) in which one or both of $R_a$ and $R_{a'}$ are groups (III) in which R is a W—$R^1$ group wherein W is a bond and $R^1$ is as defined above can be prepared according to conventional methods for the preparation of ketones, for example reaction of a compound of formula (IA) in which one or both of $R_a$ and $R_{a'}$ are groups (III) wherein R is a W—$R^1$ group in which W is O and $R^1$ is an alkyl group, typically a $C_1$-$C_4$ alkyl group with a carbanion of a compound $R^1$H.

The compounds of formula (IA) in which one or both of $R_a$ and $R_{a'}$ are groups (III) in which R is a W—$R^1$ group in which W is NH and $R^1$ is as defined above can be prepared according to conventional methods for the preparation of amides, by reaction of a compound of formula (IA) in which one or both of $R_a$ and $R_{a'}$ are groups (II) with an amine $R^1$—$NH_2$ or with an amine $R^1R^{1'}$NH wherein $R^1$ and $R^{1'}$ are defined above.

The compounds of formula (IA) in which one or both of $R_a$ and $R_{a'}$ are groups (III) in which R is a W—$R^1$ group in which W is —OC(O)— and $R^1$ is as defined above can be prepared from compounds of formula (IA) in which one or both of $R_a$ and $R_{a'}$ are groups (III) in which R is OH according to conventional methods for the preparation of anhydrides, for example by reaction with an acid of formula $R^1$COOH in the presence of a dehydrating agent.

The compounds of formula (IA) in which one or both of $R_a$ and $R_{a'}$ are groups (III) in which R is a W—$R^1$ group in which W is —NHC(O)— and $R^1$ is as defined above can be prepared from a compound of formula (IA) in which one or both of $R_a$ and $R_{a'}$ are groups (II) or (III) in which R is OH or a reactive derivative thereof, preferably the chloride derivative, according to conventional methods for the preparation of dicarboxylmides, for example by reaction with an organic primary amide $R^1$CONH$_2$.

The compounds of formula (IA) wherein one or both of $R_a$ and $R_{a'}$ are groups (III) wherein R is a W—$R^1$ group in which W is as defined above $R^1$ is $R^A$—$R_H$=$CH_2$, with $R^A$ being selected from any one of groups (j)-(jj) as defined above, can also be synthesised by reaction of a compound of formula (IA) in which one or both $R_a$ and $R_{a'}$ are groups (II) or (III) in which R is a hydroxy group or a reactive derivative thereof, preferably the chloride derivative, with suitable precursors of the $R^A$—$R_H$=$CH_2$ moiety, following a reaction scheme similar to that descried below for the preparation of analogous compounds in which one or both of $R_a$ and $R_{a'}$ are groups (IV).

The compounds of formula (IA) in which one or both of $R_a$ and $R_{a'}$ are groups (IV) in which R' is hydrogen can be prepared by reduction of block polymers of formula (I) in which one or both of $R_a$ and $R_{a'}$ are groups (III) in which R is a hydroxy group or a W—$R^1$ group wherein W is oxygen and $R^1$ is an alkyl group, typically a $C_1$-$C_4$ straight or branched alkyl group, preferably an ethyl group; preferably, the reduction is carried out with a metal hydride, typically LiAlH$_4$ or NaBH$_4$, in an appropriate solvent, such as an alcohol, preferably methanol or ethanol, an ether or a glycol, preferably diethylether or diglyme. As an alternative, the reduction can be carried out under hydrogen pressure in the presence of a homogeneous or heterogeneous metal-supported catalyst; preferred catalysts are those based on metals of the VIII group of the Periodic Table, preferably Pt, Rh, Ru, more preferably carbon-supported ruthenium. This reduction method is disclosed in U.S. Pat. No. 7,132,574 to Solvay Solexis.

The compounds of formula (IA) in which one or both of $R_a$ and $R_{a'}$ are groups (IV) in which R' is hydrogen can in turn be used as precursors of compounds of formula (IA) in which one or both of Ra and Ra' are groups (IV) in which R' is a $(CHR^2CHR^3O)_m$—$R_4$ group. For the preparation of the compounds in which m is 0, a compound of formula (IA) in which one or both of $R_a$ and $R_{a'}$ are groups (IV) in which R' is hydrogen is directly submitted to a reaction that allows the insertion of a group of formula $R^4$ other than hydrogen, while for the preparation of the block copolymers in which R' is a $(CHR^2CHR^3O)_m$—$R_4$ group wherein m is higher than 1, a block copolymer of formula (IA) in which one or both of $R_a$ and $R_{a'}$ are groups (IV) in which R' is hydrogen is first reacted with ethylene oxide, propylene oxide, ethylene carbonate or propylene carbonate in the presence of an inorganic or organic base catalyst, for example an alkaline or terrous-alkaline hydroxide, or a tertiary amine, to provide a block copolymer of formula (IA) wherein one or both of $R_a$ and $R_{a'}$ are groups (IV) wherein R' is $(CHR^2CHR^3O)_m$—$R^4$ with $R^4$ being hydrogen. This block copolymer is then submitted to a reaction that allows the introduction of the $R^4$ group. Examples of reactions that allow the introduction of a $R^4$ group other than hydrogen are described below in greater detail.

The synthesis of compounds of formula (IA) in which one or both of $R_a$ and $R_{a'}$ are groups (IV) in which R' is a $(CHR^2CHR^3O)_m$—$R^4$ in which $R^4$ is a hydrocarbon chain, a cycloaliphatic, an alkylcycloaliphatic, an aromatic or an alkylaromatic group as defined above can be prepared by transforming the hydroxy group in a compound of formula (IA) in which one or both of $R_a$ and $R_{a'}$ are groups (IV) in which R' is a $(CHR^2CHR^3O)_m$ group wherein $R^4$ is hydrogen into a leaving group, such as a nonaflate, a triflate or a tosylate group, followed by reaction with a reactive compound containing a $R^4$ group, typically an alcoholate. As an alternative, the hydroxy group can be transformed into an alkoxy group and reacted with an alcohol $R^4OH$ in which the hydroxy group has been transformed into a leaving group, such as a nonaflate, triflate or tosylate.

The compounds of formula (IA) in which one or both of $R_a$ and $R_{a'}$ are groups (IV) in which R' is a $(CHR^2CHR^3O)_m$—$R^4$ group with $R^4$ being a $P(O)R^5R^6$ group, in which $R^5$ and $R^6$ are as defined above, can be prepared, for instance, by reacting a block copolymer of formula (I) in which one or both of $R_a$ and $R_{a'}$ are groups (IV) in which R' is hydrogen or a $(CHR^2CHR^3O)_m$—$R^4$ group with m equal to or higher than 1 and $R^4$ being hydrogen with phosphoryl trichloride ($POCl_3$) in the presence of a base as HCl acceptor or with phosphorus pentoxide ($P_2O_5$) or with pyrophosphoric acid or with a polyphosphoric acid, and optionally salifying the resulting compound.

The compounds of formula (IA) in which one or both of $R_a$ and $R_{a'}$ are groups (IV) in which R' is a $(CHR^2CHR^3O)_m$—$R^4$ group with $R^4$ being a $COR^7$ group as defined above can be prepared by reaction of a compound of formula (I) in which one or both of $R_a$ and $R_{a'}$ are groups (IV) in which R' is hydrogen or a $(CHR^2CHR^3O)_m$—$R^4$ group wherein m is higher than 1 and $R_4$ is hydrogen with a carboxylic acid $R^7CO_2H$ or with a reactive derivative thereof; for the purposes of the present description, the expression "reactive derivative" of carboxylic acids is meant to comprise chlorides, bromides, iodides and esters.

The compounds of formula (IA) in which one or both of $R_a$ and $R_{a'}$ are groups (IV) in which R' is a $(CHR^2CHR^3O)_m$—$R^4$ group with $R^4$ being a $CONHR^8$ group wherein $R^8$ is the same as $R^7$ can be prepared by reacting a compound of formula (IA) in which one or both of $R_a$ and $R_{a'}$ are groups (IV) in which R' is hydrogen or a $(CHR^2CHR^3O)_m$—$R^4$ group wherein m is equal to or higher than 1 and $R^4$ is hydrogen with an isocyanate $R^8$—N=C=O. The compounds of formula (IA) in which one or both of $R_a$ and $R_{a'}$ are groups (IV) in which R' is a $(CHR^2CHR^3O)_m$—$R^4$ group with $R^4$ being a $CONHR^8$ group wherein $R^8$ is a $COR^7$ group can be prepared by reaction of a compound of formula (IA) in which one or both of $R_a$ and $R_{a'}$ are groups (IV) in which R' is hydrogen or a $(CHR^2CHR^3O)_m$—$R^4$ group wherein m is equal to or higher than 1 and $R^4$ is hydrogen with dichlorocarbonate and by reacting the resulting compound with an amide of formula $R^7CONH_2$.

The compounds of formula (IA) in which one or both of $R_a$ and $R_{a'}$ are groups (IV) in which R' is a $(CHR^2CHR^3O)_m$—$R^4$ group with $R^4$ being a CO—$R^A$—$CR_H$=$CH_2$ group in which $R^A$ is —NH—$R^B$—O—CO— a can be prepared by reaction of a compound (IA) in which one or both of $R_a$ and $R_{a'}$ are groups (IV) in which R' is hydrogen or a $(CHR^2CHR^3O)_m$—$R^4$ group wherein m is equal to or higher than 1 and $R^4$ is hydrogen with dichlorocarbonate, followed either by reaction with an amine of formula $NH_2$—$R^B$—O—CO—$CR_H$=$CH_2$ or by reaction of an aminoalcohol $NH_2$—$R^B$—OH, followed by reaction with a carboxylic acid of formula $CH_2$=$CR_HCO_2H$ or with a reactive derivative thereof.

The compounds of formula (IA) in which one or both of $R_a$ and $R_{a'}$ are groups (IV) in which R' is a $(CHR^2CHR^3O)_m$—$R^4$ group with $R^4$ being a CO—$R^A$—$CR_H$=$CH_2$ group in which $R^A$ is NH—$R^B$—NHCOO—$R^B$—OCO—, wherein $R^B$ is as defined above, can be prepared by reaction of a compound (IA) in which one or both of $R_a$ and $R_{a'}$ are groups (IV) in which R' is hydrogen or a $(CHR^2CHR^3O)_m$—$R^4$ group with m equal to or higher than 1 and $R^4$ being hydrogen with dichlorocarbonate, followed by reaction with a diamine $NH_2$—$R^B$—$NH_2$ to provide an intermediate in which one or both of $R_a$ and $R_{a'}$ comply with formula ($CF_2CF_2CF_2O)_nCH_2CF_2CH_2$ $OCONHR^BNH_2$. This intermediate can be further reacted with dichlorocarbonate and a diol HO—$R^B$—OH to provide a further intermediate in which one or both of $R_a$ and $R_{a'}$ comply with formula $(CF_2CF_2CF_2O)_n$ $CH_2CF_2CH_2OCONHR^BNHCOOR^B$—OH which, by reaction with a carboxylic acid of formula $CH_2$=$CRHCO_2H$ or with a reactive derivative thereof, affords the aforementioned compound (IA).

The compounds of formula (IA) in which one or both of $R_a$ and $R_{a'}$ are groups (IV) in which R' is a $(CHR^2CHR^3O)_m$—$R^4$ group with $R^4$ being a CO—$R_A$—$CR_H$=$CH_2$ group in which $R_A$ is $R^B$—O—CO— can be prepared by reaction of a compound of formula (IA) in which one or both of $R_a$ and $R_{a'}$ are groups (IV) in which R' is hydrogen or a $(CHR^2CHR^3O)_m$—$R^4$ group wherein m is equal to or higher than 1 and $R^4$ is hydrogen with an acid of formula $CH_2$=$CR_H$—$R^A$—$CO_2H$ or with a reactive derivative thereof; as an alternative, a compound of formula (IA) in which one or both of $R_a$ and $R_{a'}$ are groups (IV) in which R' is hydrogen or a $(CHR^2CHR^3O)_m$—$R^4$ group wherein m is equal to or higher than 1 and $R^4$ is hydrogen can be reacted with a hydroxy acid PO—$R^B$—COOH, wherein P is a hydroxy-protecting group, or with a reactive derivative thereof, to provide an intermediate in which one or both of $R_a$ and $R_{a'}$ comply with formula $(CF_2CF_2CF_2O)_nCH_2$ $CF_2CH_2O(CHR^2HR^3O)_mCOR^B$—OP which, after removal of the protecting group and reaction with a carboxylic acid $CH_2$=$CHR_H$—COOH or with a derivative thereof, affords the desired aforementioned compound (IA).

The compounds of formula (IA) in which one or both of $R_a$ and $R_{a'}$ are groups (V) as defined above can be prepared by fluorinating a compound of formula (I) in which one or both of $R_a$ and $R_{a'}$ are groups (III) as defined above, wherein R is a hydroxy group. The reaction is typically carried out in a fluorinated solvent selected from (per)fluoroalkyl compounds and hydrofluoroethers, such as perfluorobutyl tetrahydrofurane, perfluoropropyl tetrahydropyrane, Vertrel® XF 2,3-dihydrodecafluoropentane, or HFE® 7100 methoxynonafluorobutane, at a temperature ranging preferably from −40 to +30° C., more preferably from −30 to +10° C., even more preferably from −30 to 0° C., bubbling fluorine, optionally diluted in helium, at a molar ratio of from 1:1 to 1:0.01.

The compounds of formula (IA) in which one or both of $R_a$ and $R_{a'}$ are groups (VI) as defined above can be prepared by hydrogenation of a compound of formula (I) in which one or both of $R_a$ and $R_{a'}$ are groups (III) as defined above, wherein R is a hydroxy group. The reaction is typically carried out in a solvent selected from ethers and glycols, preferably glyme, at a temperature ranging preferably from 150° C. to 250° C., more preferably from 180° C. to 220° C., in the presence of an excess of an organic or inorganic base, such as $NH_4OH$, KOH, NaOH and CsOH.

The block copolymers of formula (IIB) can be prepared by reaction of a compound of formula (IA) in which one or both of $R_a$ and $R_{a'}$ are groups (II) as defined above in which R' is either hydrogen or a $(CHR^2CHR^3O)_m$—$R^4$ group in which $R^2$ and $R^3$ are as defined above, m is 1 or an integer higher than 1 and $R^4$ is hydrogen with hexafluorotriphosphazene or octachlorotetraphosphazene. Typically, the aforementioned compound (IA) is dissolved in a fluorinated or hydrofluorinated solvent with a boiling point ranging from 20 to 150° C., preferably from 40 to 100° C., such as perfluorobutyl tetrahydrofurane or perfluoropropyl tetrahydropyrane; hexafluorotriphosphazene or octachlorotetraphosphazene is usually added to the reaction mixture in the form of an alkaline solution. The reaction is usually carried out at a temperature ranging from room temperature to 100° C., preferably from 40 to 80° C., more preferably form 60 to 80° C. For the preparation of compounds (IIB) in which $q_z$ is an integer ranging from 1 to 5 or 1 to 7, the reaction product is salified with an appropriate compound.

The block copolymers of the invention, in particular the compounds of formula (IA) in which one or both of $R_a$ ad $R_{a'}$ contain an acrylate moiety, in particular a methacrylate moiety, are characterised by low surface energy, high chemical resistance and they are able to impart to materials and coatings self-cleaning properties and oil-repellence properties; therefore a further object of the present invention is the use of the block copolymers of the invention as water- and oil-resistance agents.

Water and oil resistance compositions containing one or more block copolymers of the invention in admixture with additives or vehicles are a still further object of the invention.

The block copolymers of the invention and the compositions containing them can be applied to a variety of substrates, such as glass or cellulose substrates, especially those used in packaging applications.

The block copolymers of formula (IA) in which one or both of $R_a$ and $R_{a'}$ contain an acrylate function can advantageously be used in nanolithography processes for reproducing (nano) patterns using flexible moulds; for this purpose, the compounds (IA) are applied to a patterned template surface and submitted to UV radiations in the presence of a photoinitiator. A non exhaustive list of photoinitiators and their amounts is reported, for example, in EP 2221664 A (SOLVAY S.A.).

The block copolymers of the invention, in particular the compounds of formula (IA) in which one or both of $R_a$ and $R_{a'}$ are groups (V) or (VI) as defined above are endowed with improved lubricant properties. Furthermore, the block copolymers of the invention are advantageous in that they can be used without anti-wear additives, which need usually be added to (per)fluorinated oils. Particularly advantageous are the compounds of formula (IA) in which:
  chain $R_f$ complies with formula —$(CF_2CF_2O)_{p'}(CF_2O)_{q'}$—, wherein p' and q' are integers ≥0 and are selected in such a way as they comply with the above-mentioned molecular weight requirement;
  $R_a$ is a group of formula (V) or (VI) as defined above in which n ranges from 5 to 15; and
  $R_{a'}$ is the same as $R_a$.

Therefore, a further object of the invention is the use of the block copolymers of the invention as lubricants.

Lubricant compositions containing one or more block copolymers of the invention are a still further object of the invention.

The block copolymers of the invention can also be advantageously used as co-macromers, in particular those containing an acrylate moiety, for the synthesis of other polymers, or for the preparation of fluorinated coatings. Furthermore, the block copolymers of the invention can be used for preparing surface modifiers or surface-treating agents.

The following examples illustrate the invention in greater detail without limiting its scope.

Should the disclosure of any patents, patent applications and publications which are herein incorporated by reference be in conflict with the present application to the extent that it may render a term unclear, the present description shall take precedence.

PREPARATIVE EXAMPLES

Raw Materials 2,2,3,3-Tetrafluoroxethane was prepared from ethylene and formaldehyde according to known methods. (Per)fluoropolyethers acyl precursors were synthesised according to the procedure disclosed in U.S. Pat. No. 3,847,978 (MONTEDISON SPA), U.S. Pat. No. 4,755,330 (AUSIMONT SPA), U.S. Pat. No. 4,755,330 (AUSIMONT SPA), U.S. Pat. No. 6,919,479 (SOLVAY SOLEXIS SPA). The other chemicals and solvents are commercially available; in some instances, solvents were distilled before use.

In the following examples, $R_{f'}$ stands for —$OCF_2CF_2O(CF_2CF_2O)_p(CF_2O)_qCF_2CF_2O$; p/q=2

Example 1

Synthesis of $R_{f'}[(CH_2CF_2CF_2O)_{7.2}CH_2CF_2COOH]_2$

A 100 ml, 3-necked flask, kept under nitrogen and equipped with a magnetic stirrer, a thermometer, a condenser and a dropping funnel, was charged with ethylenglicol dimethyl ether (16 ml), CsF (0.63 g; 4.2 meq), the diacyl fluoride $F(O)CCF_2O(CF_2CF_2O)_p(CF_2O)_qCF_2C(O)F$ (16 g; Mw=1477; Ew=770 p/q=2), 23 g of 2,2,3,3-tetrafluorooxethane (Mw=130) and stirred at 30° C.

After 3 hours, $^{19}$FNMR analysis of the crude mixture confirmed the complete reaction of the added monomer by monitoring the absence of its typical signals (−80 ppm and −120 ppm), The reaction mixture was added with water and left under stirring for 1 hour in order to allow the title compound to separate.

The resulting mixture was then poured in a separator funnel and the lower phase was separated and distilled to afford 35 gr of the title compound $R_{f'}$ [$(CH_2CF_2CF_2O)_{7.2}CH_2CF_2COOH]_2$ as residue.

Example 2

Synthesis of $R_{f'}[(CH_2CF_2CF_2O)_4CH_2CF_2COOH]_2$

A 100 ml, 3-necked flask, kept under nitrogen and equipped with a magnetic stirrer, a thermometer, a condenser and a dropping funnel was charged with ethylenglicol dimethyl ether (6 ml), CsF (2.65 g; 17.7 meq), the diacylfluoride $F(O)CCF_2O(CF_2CF_2O)_p(CF_2O)_qCF_2COF$ (20 g; Mw=432; Ew=229 p/q=2), 56.8 g of 2,2,3,3-tetrafluorooxethane (Mw=130) and stirred at 30° C.

After 3 hours, $^{19}$FNMR analysis of the crude mixture confirmed the complete reaction of the added monomer by monitoring the absence of its very typical signals (−80 ppm and −120 ppm).

The reaction mixture was added with water and left under stirring for 1 hour in order to allow the title compound to separate.

The resulting mixture was then poured in a separator funnel and the lower phase was separated; distillation of the lower phase afforded 56 gr of the title compound $R_f[(CH_2CF_2CF_2O)_4CH_2CF_2COOH]_2$ as residue.

Example 3

Synthesis of $R_f[(CHXCF_2CF_2O)_{7.2}CHXCF_3]_2$

A stainless steel reactor was charged with 300 g of a 5% (w/w) solution of the compound of example 1 in Galden A® perfluoropolyether and cooled to −25° C. The solution, kept under vigorous stirring, was then bubbled with a stream of $F_2$ diluted in helium (He:$F_2$=5:1 molar).

The reaction was checked by retrieving a solution sample, evaporating the solvent and analyzing the residue and monitoring by $^{19}$NMR analysis the disappearance of the preterminal CH$_2$CF$_2$COOH signal at −115 ppm an the appearance of a new signal at −75 ppm, attributed to the newly formed $CF_3$ end group. The reaction was considered completed when the conversion of the carboxylic acid was higher than 99%.

The reaction mixture was then bubbled with helium, let to warm to room temperature and distilled; 12.5 gr of $R_f[(CHXCF_2CF_2O)_{7.2}CHXCF_3]_2$ (with H/X=4.1) were recovered as residue.

Example 4

Synthesis of $R_f[(CH_2CF_2CF_2O)_{7.2}CH_2CF_2H]_2$

A 100 ml, 3-necked flask, kept under nitrogen and equipped with a magnetic stirrer, a thermometer, a condenser and a dropping funnel was charged with 15 ml of diethylenglicol, 15 g of the compound of example 1 and 3 g of KOH (50% aqueous solution). The resulting mixture was the heated up to 180° C. and let to stir for 8 hours.

The conversion of the reaction was checked monitoring by $^{19}$FNMR analysis of the crude mixture the disappearance of the preterminal CH$_2$CF$_2$COOH signal at −114 ppm and the formation of a new signal at −130 ppm, attributed to the newly formed CF$_2$H end group. The reaction was considered completed when the conversion of the carboxylic acid was >99%.

The reaction mixture was then brought to room temperature, added with 15 g of HCl (10% aqueous solution) and let to stir for 1 hour. The resulting mixture was then poured in a separator funnel and the lower phase was submitted to distillation to afford 13.2 gr title product $R_f[(CH_2CF_2CF_2O)_{7.2}CH_2CF_2H]_2$ as distillation residue.

Example 5

Synthesis of $R_f[(CHXCF_2CF_2O)_4CHXCF_3]_2$

A stainless steel reactor was charged with 300 g of a 5% (w/w) solution of the compound of example 2 in Galden A® perfluoropolyether and cooled to −25° C. The solution, kept under vigorous stirring, was then bubbled with a stream of $F_2$ diluted in helium (He:$F_2$=5:1 molar).

The conversion was checked by retrieving a solution aliquot, evaporating the solvent and analyzing the residue and monitoring by $^{19}$NMR analysis the disappearance of the preterminal CH$_2$CF$_2$COOH signal at −114 ppm and the formation of a new signal at −75 ppm attributed to the newly formed CF$_3$ end group. The reaction was considered completed when the conversion of the carboxylic acid was higher than 99%.

The reaction mixture was then bubbled with helium, let to warm to room temperature and distilled; 12.0 gr of title product $R_f[(CHXCF_2CF_2O)_4CHXCF_3]_2$ (with H/X=4.0) were recovered as residue.

Example 6

Synthesis of $R_f[(CH_2CF_2CF_2O)_5CH_2CF_2COOH]_2$

A 100 ml, 3-necked flask, kept under nitrogen and equipped with a magnetic stirrer, a thermometer, a condenser and a dropping funnel was charged with 16 ml of ethylenglicol dimethyl ether, 1.3 g of CsF (Mw=152), 16 g of the diacylfluoride F(O)CCF$_2$O(CF$_2$CF$_2$O)$_p$(CF$_2$O)$_q$CF$_2$COF (Mw=704; Ew=382 p/q=2.2), 33 g of 2,2,3,3-tetrafluorooxethane (Mw=130) and let to stir at 30° C.

After 3 hours, $^{19}$FNMR analysis of the crude mixture confirmed the complete reaction of 2,2,3,3-tetrafluorooxethane (absence of its typical signals at −80 ppm and −120 ppm.

The reaction mixture was added with 15 g water and let to stir for 1 hour in order to allow the title product to separate from the reaction mixture.

The resulting mixture was then poured in a separator funnel and the lower phase was separated and distilled, to afford 47 gr of the title product as distillation residue.

Example 7

Synthesis of $R_f[(CH_2CF_2CF_2O)_5CH_2CF_2COOEt]_2$

A 100 ml, 3-necked flask, kept under nitrogen and equipped with a magnetic stirrer, a thermometer, a condenser and a dropping funnel was charged with 16 ml ethylenglicol dimethyl ether, 1.3 g CsF (Mw=152), 16 g diacylfluoride F(O)CCF$_2$O(CF$_2$CF$_2$O)$_p$(CF$_2$O)$_q$CF$_2$COF (Mw=704; Ew=382 p/q=2.2), 33 g 2,2,3,3-tetrafluorooxethane (Mw=130) and let to stir at 30° C.

The reaction mixture was added with 20 g of anhydrous ethanol and let to stir for 1 hour.

The resulting solution was then poured in a separator funnel containing water and the lower phase was separated and submitted to distillation; 48 g title product were recovered as distillation residue.

Example 8

Synthesis of $R_f[(CH_2CF_2CF_2O)_5CH_2CF_2CH_2OH]_2$

A 100 ml, 3-necked flask, kept under nitrogen and equipped with a magnetic stirrer, a thermometer, a condenser and a dropping funnel, was charged with 40 ml anhydrous ethanol and 1.1 g of NaBH$_4$ (Mw=40); the resulting solution was then cooled to 5° C. and 30 g of the compound of example 7 $R_f[(CH_2CF_2CF_2O)_5CH_2CF_2COOEt]_2$ (Ew=1188) were slowly added keeping the temperature below 10° C.

The conversion of the reaction was checked by $^{19}$NMR analysis, monitoring the disappearance of the preterminal CH$_2$CF$_2$COOEt signal at −114 ppm and the formation of the a signal at −117 ppm, attributed to the newly formed preterminal CH$_2$CF$_2$CH$_2$OH.

The reaction was considered completed when the conversion of the carboxylic ester was higher than 98%.

The reaction mixture was then let to warm to room temperatures and added with 30 g of an aqueous solution of HCl (10%), and left under stirring for 1 hour. The resulting mixture was then poured in a separator funnel and the lower phase was separated and distilled; 27.2 g of the title product $R_f[(CH_2CF_2CF_2O)_5CH_2CF_2CH_2OH]_2$ were recovered as distillation residue.

Example 9
Synthesis of $R_f[(CH_2CF_2CF_2O)_5CH_2CF_2CH_2OC(O)NHCH_2CH_2OC(O)C(CH_3)=CH_2]_2$ A 100 ml, 3-necked flask, kept under nitrogen and equipped with a magnetic stirrer, a thermometer, a condenser

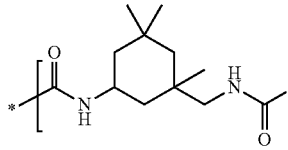

and a dropping funnel was charged with 50 ml anhydrous MEK, 30 μl of a solution of Sn dibutyl dilaurate in MEK (20% w/v) and 15 g of the compound of example 8 $R_f[(CH_2CF_2CF_2O)_5CH_2CF_2CH_2OH]_2$ (Ew=1144). The so obtained solution was then heated to 50° C. and 2.1 g of ethyl isocyanate methacrylate (Ew=155) were added and the solution was kept under stirring for 2 hours.

The reaction was followed by means of FTIR analysis, monitoring the disappearance of the typical isocyanate band at 2250 cm$^{-1}$. Moreover the conversion of the compound of example 8 was detected by $^{19}$NMR analysis, monitoring the disappearance of the preterminal $CH_2\underline{CF_2}CH_2OH$ at −117 ppm and the formation of a new signal at −115 ppm, attributed to the newly formed preterminal $CH_2\underline{CF_2}CH_2OC(O)NHCH_2CH_2OC(O)C(CH_3)=CH_2$.

The reaction was considered completed when the conversion of the alcoholic group was higher than 98%; after removing the solvent by distillation, 16.5 g of the title compound, $R_f[(CH_2CF_2CF_2O)_5CH_2CF_2CH_2OC(O)NHCH_2CH_2CH_2OC(O)C(CH_3)=CH_2]_2$, were recovered as residue.

Example 10
Synthesis of

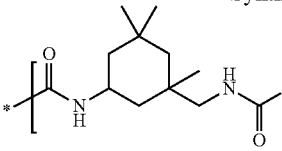

A 250 ml, 4-necked flask kept under nitrogen and equipped with a mechanical stirrer, a thermometer and a condenser was charged with 30 g of the compound of example 8 $R_f[(CH_2CF_2CF_2O)_5CH_2CF_2CH_2OH]_2$, Ew=1143), 4 g MEK, 6 g isophorone diisocyanate (IPDI, Ew=111) and 15 μl of a solution of Sn dibutyl dilaurate in MEK (20% w/v); the resulting solution was then heated up to 65° C. and left under stirring.

The reaction was checked by $^{19}$NMR analysis, monitoring the disappearance of the preterminal $CH_2\underline{CF_2}CH_2OH$ signal at −117 ppm and the appearance of a new signal at −115 ppm, attributed to the newly formed $CH_2\underline{CF_2}CH_2O\ C(O)NHR_{IPDI}$ group, wherein $R_{IPDI}$ represent the $R_{IPDI}$ moiety.

After 3 hrs the conversion of the compound of example 8 was higher than 98% and the reaction was considered completed.

The reaction mixture was then added with 14 g of a MEK solution containing 1.83 g of dimethylolpropionic acid (DMPA) and 1.1 g triethylamine (TEA, Ew=101) and left under stirring until FTIR analysis showed complete disappearance of the —NCO signal of the $R_{IPDI}$ moiety at 2250 cm$^{-1}$.

Example 11
Synthesis of

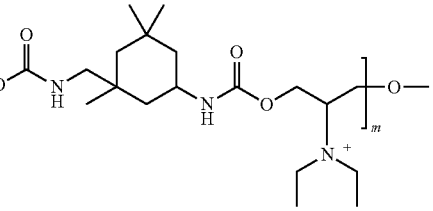

A 250 ml 4-necked flask, kept under nitrogen and equipped with a mechanical stirrer, a thermometer and a condenser, was charged with 25 g of the compound of example 8 $R_f[(CH_2CF_2CF_2O)_5CH_2CF_2CH_2OH]_2$, Ew=1143), 3 g MEK, 5 g IPDI (Ew=111) and 15 μl of a solution of Sn dibutyl dilaurate in MEK (20% w/v); the resulting solution was heated up to 65° C. and left under stirring.

The conversion of the reaction was checked by $^{19}$NMR analysis, monitoring the disappearance of the preterminal $CH_2\underline{CF_2}CH_2OH$ signal at −117 ppm and the formation of a new signal at −115 ppm, attributed to the newly CH$_2$ $\underline{CF_2}CH_2O\ C(O)NHR_{IPDI}$ group, wherein $R_{IPDI}$ represent the $R_{IPDI}$ moiety.

After 3 hrs the conversion of the compound of example 8 was higher than 98% and the reaction was considered completed.

The reaction mixture was then added with 13 g of a MEK solution containing 1.7 g diethylaminopropanediol (DEAPD; Ew OH=73.5 and left under stirring until FTIR analysis showed complete disappearance of the —NCO signal of the $R_{IPDI}$ moiety at 2250 cm$^{-1}$.

Applicative Tests
Test 1—Evaluation of Lubricant Properties

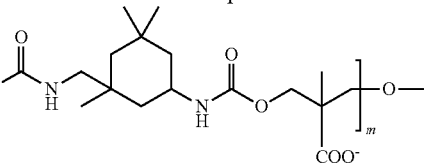

Anti-wear properties have been measured with a Tribometer SRV equipment, accordingly to ASTM 6425. The test temperature was 50° C., at 50 Hz, 1 mm stroke at 300N load for 2 h. The wear value was measured at the end of the test by visual inspection with a Motic Digital Microscope DM-143.

The results are reported in the table 1 below, in which a comparison among products obtained in examples 3 and 5 are compared with the following commercial perfluorinated oils having similar viscosity, as determined by applying the method ASTM D445:

Demnum® S65 PFPE (Daikin)

Demnum® S20 PFPE (Daikin)

Fomblin® Z03 PFPE (Solvay Solexis)

TABLE 1

Table 1

| Sample | v (cSt) 40° C. | Wear (mm) average | Std dev. |
|---|---|---|---|
| Fomblin ® Z03 PFPE | 18 | 1.15 | 0.03 |
| Product of ex. 5 | 17 | 0.64 | 0.04 |
| Product of ex. 3 | 65 | 0.75 | 0.04 |
| Demnum ® S65 PFPE | 65 | 0.86 | 0.01 |
| Demnum ® S20 PFPE | 25 | 0.96 | 0.04 |
| Fomblin ® Z03 PFPE + 4% Fomblin ® DA607 PFPE | 18 | 0.87 | 0.01 |

It stems from table 1 that the products of examples 3 and 5 of the present invention cause a significantly lower wear with respect to perfluorinated commercial products having similar viscosity. It can also be appreciated that the addition of an anti-wear additive Fomblin® DA607 PFPE to Fomblin® Z03 PFPE, reduces wear from 1.15 down to 0.87, but the latter value is nonetheless higher than the value obtained using the product of example 5 alone. (0.64).

Test 2—Evaluation of Thermal Stability

The product of example 3 has been compared with Fomblin® 03 PFPE, which has a similar MW (3700 Mw and 4000 MW, respectively). TGA analysis, performed accordingly to ASTM E-1131, evidence two overlapping phenomena: weight loss due to evaporation (always occurring when non polymeric materials undergo the typical TGA temperature excursion) and weight loss due to degradation (i.e. fragmentation to more volatile byproducts).

The data reported in table confirm that volatility/degradation of the product of example 3 is lower than that of the reference commercial product.

TABLE 2

| | Mw | Kinematic viscosity (cSt) | | | Evaporation weight loss TGA | | |
|---|---|---|---|---|---|---|---|
| | NMR | 20° C. | 40° C. | 100° C. | T 5% | T 10% | T 50% |
| Fomblin ® Z03 PFPE | 4000 | 30 | 18 | 5.6 | 196 | 247 | 304 |
| Product of ex. 3 | 3700 | — | 82 | 10.3 | 209 | 255 | 341 |

Test 3—Evaluation of Surface Properties

A Q-panel® test panel was coated with a 30 μm film obtained by radical photopolymerization of the compound of example 9 in the presence of 5% (w/w) of 2,2-dimethoxy-2-phenylacetophenone as photoinitiator, using a UV light Fusion system model VPS 1600 equipped with a 13 mm H lamp.

The surface properties of the UV-cured film was then evaluated measuring the static contact angles vs water and vs n-hexadecane of the coated Q-Panel®; the results are reported in table 3 below.

Test 4

A Q-Panel® test panel was coated with a 30 μm film obtained by radical photopolymerization of a 75/25 (w/w) formulation of the compound of example 9 with trypropylene glycol diacrylate (TPGDA) in the presence of 5% (w/w) of 2,2-dimethoxy-2-phenylacetophenone as photoinitiator, using a UV light Fusion system model VPS 1600 equipped with a 13 mm H lamp.

The surface properties of the UV-cured film were then evaluated measuring the static contact angles vs water and vs n-hexadecane of the coated Q-panel test panel; the results are reported in table 3 below.

TABLE 3

Table 3

| | θ water | θ n-hexadecane |
|---|---|---|
| Al Q-panel ® test panel | 89 ± 2 | 48 ± 2 |
| Al Q-panel ® test panel treated with the compound of example 9 | 105 ± 1 | 57 ± 1 |
| Al Q-panel ® test panel treated with the compound of example 9 and TPGDA (75/25) | 103 ± 1 | 56 ± 1 |

The invention claimed is:

1. A process for the preparation of a (per)fluoropolyether block copolymer, the block copolymer comprising:
   A) a fluoropolyoxyalkylene segment (chain $R_a$) comprising one or more units of formula $(CHXCF_2CF_2O)$— in which X is hydrogen or fluorine; and
   B) a (per)fluoropolyoxyalkylene segment (chain $R_f$), wherein chain $R_f$ complies with formula:

$$—(CF_2CF_2O)_{p'}(CF_2O)_{q'}—$$

wherein p' and q' are integers ≥0 and are selected in such a way that chain $R_f$ has a molecular weight greater than 400 g/mol,
   said process comprising ring-opening a 2,2,3,3-tetrafluorooxethane with an acyl fluoride of a (per)fluoropolyether comprising chain $R_f$ in the presence of an inorganic or organic fluoride.

2. The process according to claim 1, wherein the (per)fluoropolyether block copolymer complies with formula (IA):

$$R_a—R_f—R_{a'} \tag{IA}$$

wherein chain $R_f$ is as defined in claim 1 and chain $R_a$ is selected from:
   a group (II) of formula:

$$(CH_2CF_2CF_2O)_nCH_2CF_2C(O)F \tag{II}$$

wherein n is an integer equal to or higher than 1;
   a group (III) of formula:

$$(CH_2CF_2CF_2O)_nCH_2CF_2C(O)R \tag{III}$$

wherein
      n is as defined above, and
      R is hydrogen a hydroxy group or a W—$R^1$ group in which W is a bond or is selected from —O—, —NH—, —OC(O)—, and —NHC(O)—; and $R^1$ is selected from: a straight or branched, saturated or unsaturated ($C_1$-$C_{36}$)hydrocarbon chain; a ($C_5$-$C_{14}$)cycloalkyl or ($C_5$-$C_{14}$)cycloalkyl($C_1$-$C_{10}$) alkyl group, the cycloalkyl moiety being optionally substituted with one or more ($C_1$-$C_4$)straight or branched alkyl chains; a ($C_6$-$C_{14}$)aryl or ($C_1$-$C_{10}$) alkyl($C_6$-$C_{14}$)aryl group; and a group of formula —$R^4$—$CR_H$=$CH_2$ in which $R_H$ is hydrogen or a ($C_1$-$C_{34}$)straight or branched, saturated or unsaturated hydrocarbon chain and $R^4$ is selected from:

$$—NH—R^B—O—CO—; \tag{j}$$

$$—NH—R^B—NHCOO—R^B—OCO—; \text{ and} \tag{jj}$$

$$—R^B—O—CO—; \tag{jjj}$$

$R^B$ being a divalent group selected from: a $(C_1$-$C_{10})$ aliphatic group, a $(C_5$-$C_{14})$cycloaliphatic group, a $(C_6$-$C_{14})$aromatic, or a $(C_1$-$C_{10})$alkyl$(C_6$-$C_{14}$aryl) group;

a group (IV) of formula:

$$(CH_2CF_2CF_2O)_nCH_2CF_2CH_2OR' \qquad (IV)$$

wherein n is as defined above and R' is hydrogen or a $(CHR^2CHR^3O)_m$—$R^4$ group in which:

$R^2$ and $R^3$ are both hydrogen or one is hydrogen and the other is methyl;

m is 0 or an integer equal to or higher than 1;

$R^4$ is selected from hydrogen, with the proviso that, when m is 0, $R^4$ is not hydrogen; a straight or branched, saturated or unsaturated $(C_1$-$C_{36})$hydrocarbon chain; a $(C_5$-$C_{14})$cycloaliphatic or $(C_1$-$C_{10})$alkyl$(C_5$-$C_{14})$cycloalkyl group; a $(C_6$-$C_{14})$aromatic or $(C_1$-$C_{10})$alkyl$(C_6$-$C_{14})$aromatic group; a $P(O)R^5R^6$ group, in which $R^5$ and $R^6$ are, independently of each other, selected from hydroxy and —O⁻X⁺ groups, in which X⁺ is selected from Li⁺, Na⁺, K⁺, $(NH_3R')^+$, $(NH_2R'R'')^+$ and $(NHR'R''R''')^+$ wherein R is H or a linear or branched $(C_1$-$C_{22})$alkyl group optionally containing one or more —OH groups, and R', R'' and R''', equal to or different from each other, are linear or branched $(C_1$-$C_{22})$alkyl groups optionally containing one or more —OH groups or optionally linked to each other to form N-heterocyclic groups; a $COR^7$ group, in which $R^7$ is selected from a straight or branched, saturated or unsaturated $(C_1$-$C_{36})$hydrocarbon chain; a $(C_5$-$C_{14})$cycloaliphatic or $(C_1$-$C_{10})$alkyl$(C_5$-$C_{14})$cycloalkyl group; a $(C_6$-$C_{14})$aromatic or $(C_1$-$C_{10})$alkyl$(C_6$-$C_{14})$aromatic group; a $CONHR^8$ group, in which $R^8$ is the same as $R^7$; a $COR^7$ group, in which $R^7$ is as defined above; and a CO—$R^A$—$CR_H$=$CH_2$ group, wherein $R_H$ is hydrogen or a straight or branched, saturated or unsaturated $(C_1$-$C_{34})$hydrocarbon chain and $R^A$ is selected from:

—NH—$R^B$—O—CO—;      (j)

—NH—$R^B$—NHCOO—$R^B$—OCO—; and      (jj)

—$R^B$—O—CO—;      (jjj)

$R^B$ being a divalent group selected from a $(C_1$-$C_{10})$ aliphatic group, a $(C_5$-$C_{14})$cycloaliphatic group, a $(C_6$-$C_{14})$aromatic group or a $(C_1$-$C_{10})$aliphatic $(C_6$-$C_{14})$aromatic group;

a group (V) of formula:

$$(CHYCF_2CF_2O)_nCHYCF_3 \qquad (V)$$

wherein n is as defined above and Y is fluorine or hydrogen; and a group (VI) of formula:

$$(CH_2CF_2CF_2O)_nCH_2CF_2H \qquad (VI)$$

wherein n is as defined above;

and wherein $R_{a'}$ is the same as $R_a$ or is a $(C_1$-$C_5)$(per)fluoroalkyl group optionally containing hydrogen and/or chlorine atoms.

3. The process according to claim 2, wherein $R^7$ is selected from a —$CR_H$=$CH_2$ chain, wherein $R_H$ is hydrogen or a straight or branched, saturated or unsaturated $(C_1$-$C_{34})$hydrocarbon chain; a $(C_5$-$C_{14})$cycloaliphatic or $(C_1$-$C_{10})$alkyl$(C_5$-$C_{14})$cycloalkyl group; and a $(C_6$-$C_{14})$aromatic or $(C_1$-$C_{10})$alkyl$(C_6$-$C_{14})$aromatic group.

4. The process according to claim 1, wherein the ratio of p/q is 2.

* * * * *